(12) United States Patent
Weldon et al.

(10) Patent No.: US 6,468,290 B1
(45) Date of Patent: Oct. 22, 2002

(54) TWO-PLANAR VENA CAVA FILTER WITH SELF-CENTERING CAPABILITIES

(75) Inventors: James Weldon, Roslindale; Naroun Suon, Lawrence, both of MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/587,404

(22) Filed: Jun. 5, 2000

(51) Int. Cl.[7] .............................................. A61M 29/00
(52) U.S. Cl. ....................................... 606/200; 606/127
(58) Field of Search ................................ 606/200, 127, 606/108, 113, 114, 128

(56) References Cited

U.S. PATENT DOCUMENTS

| | | |
|---|---|---|
| 3,540,431 A | 11/1970 | Mobin-Uddin et al. |
| 3,952,747 A | 4/1976 | Kimmell, Jr. |
| 4,425,908 A | 1/1984 | Simon |
| 4,494,531 A | 1/1985 | Gianturco |
| 4,619,246 A | 10/1986 | Molgaard-Nielson et al. |
| 4,643,184 A | 2/1987 | Mobin-Uddin |
| 4,655,771 A | 4/1987 | Wallsten |
| 4,688,553 A | 8/1987 | Metals |
| 4,727,873 A | 3/1988 | Mobin-Uddin |

(List continued on next page.)

FOREIGN PATENT DOCUMENTS

| | | |
|---|---|---|
| EP | 0 472 334 A1 | 2/1982 |
| EP | 0 348 295 A1 | 12/1989 |
| EP | 0 430 848 A1 | 5/1991 |
| EP | 0 437 121 A2 | 7/1991 |
| EP | 0 462 008 A1 | 12/1991 |
| FR | 8909642 | 7/1989 |
| FR | 2 649 884 | 1/1991 |
| GB | 3417738 | 11/1985 |
| GB | 2 200 848 A | 8/1988 |
| GB | 2 200 848 B | 2/1991 |
| SU | 835447 | 5/1979 |
| SU | 1103868 A | 7/1983 |
| SU | 955912 A | 2/1988 |
| WO | WO 91/04716 | 4/1991 |
| WO | WO 91/11972 | 8/1991 |
| WO | WO95/08567 | 4/1995 |
| WO | WO 95/27448 | 10/1995 |
| WO | WO 96/17634 | 6/1996 |

OTHER PUBLICATIONS

Kraimps et al., "Conical Endocaval Filters with metallic Struts: Search for a New Model", 3/92, Ann. Vasc. Surg., 6:99–110.

Kraimps et al., "Optimal Central Trapping (OPCETRA) Vena Caval Filter: Results of Experimental Studies", 11/92, J. of Vasc. and Inter. Rad., 3:697–701.

Primary Examiner—Kevin T. Truong
(74) Attorney, Agent, or Firm—Crompton, Seager & Tufte LLC

(57) ABSTRACT

A self-centering filter is useful for trapping blood clots, reducing their size and arresting their further migration from the vena cava into pulmonary circulation. The two-planar filter design is formed from a conical array of filter wires wherein two sets of filter wires are included, each set differing in length from the other. The filter wires diverge from a common apex at one end and extend radially outwardly therefrom to an attachment end attachable to the wall of a blood vessel such that the attachment ends of the first set of wires are anchored at a location spaced apart from the location of anchoring of the attachment ends of the second set, effecting a two-planar filter design. This establishes a single filtering element having two planes of contact with the vein wall which also provides for centering of the filtering element. At least one of the sets of wires contains barbs, e.g. hooks, for anchoring the filter to the inner venal wall.

6 Claims, 4 Drawing Sheets

U.S. PATENT DOCUMENTS

| | | |
|---|---|---|
| 4,781,177 A | 11/1988 | Lebigot |
| 4,793,348 A | 12/1988 | Palmaz |
| 4,817,600 A | 4/1989 | Herms et al. |
| 4,830,003 A | 5/1989 | Wolff et al. |
| 4,832,055 A | 5/1989 | Palestrant |
| 4,856,516 A | 8/1989 | Hillstead et al. |
| 4,873,978 A | 10/1989 | Ginsberg |
| 4,943,297 A | 7/1990 | Saveliev et al. |
| 4,954,126 A | 9/1990 | Wallsten |
| 4,957,501 A | 9/1990 | Lahille et al. |
| 4,969,891 A | 11/1990 | Gewertz |
| 4,990,156 A | 2/1991 | Lefebvre |
| 5,059,205 A | 10/1991 | El-Nounou et al. |
| 5,061,275 A | 10/1991 | Wallsten et al. |
| 5,071,407 A | 12/1991 | Termin et al. |
| 5,108,418 A | 4/1992 | Lefebvre |
| 5,108,419 A | 4/1992 | Reger et al. |
| 5,133,733 A | 7/1992 | Rasmussen et al. |
| 5,135,516 A | 8/1992 | Sahatjian et al. |
| 5,152,777 A | 10/1992 | Goldberg et al. |
| 5,160,342 A | 11/1992 | Reger et al. |
| 5,190,546 A | 3/1993 | Jervis |
| 5,221,261 A | 6/1993 | Termin et al. |
| 5,224,953 A | 7/1993 | Morgentaler |
| 5,300,086 A | 4/1994 | Gory et al. |
| 5,304,121 A | 4/1994 | Sahatjian |
| 5,304,200 A | 4/1994 | Spaulding |
| 5,324,304 A | 6/1994 | Rasmussen |
| 5,329,942 A | 7/1994 | Gunther et al. |
| 5,344,427 A | 9/1994 | Cottenceau et al. |
| 5,370,657 A | 12/1994 | Irie |
| 5,375,612 A | 12/1994 | Cottenceau et al. |
| 5,382,261 A | 1/1995 | Palmez |
| 5,405,377 A | 4/1995 | Cragg |
| 5,476,508 A | 12/1995 | Amstrup |
| 5,522,822 A | 6/1996 | Phelps et al. |
| 5,549,629 A | 8/1996 | Miller et al. |
| 5,683,411 A | 11/1997 | Kavteladze et al. |
| 5,709,704 A | 1/1998 | Nott et al. |
| 5,800,457 A * | 9/1998 | Gelbfish ............... 606/200 |
| 5,836,968 A * | 11/1998 | Simon et al. ............... 606/200 |
| 5,836,969 A | 11/1998 | Kim et al. |
| 6,013,093 A | 1/2000 | Nott et al. |

\* cited by examiner

US 6,468,290 B1

TWO-PLANAR VENA CAVA FILTER WITH SELF-CENTERING CAPABILITIES

FIELD OF THE INVENTION

This invention relates generally to filter devices useful for trapping blood clots and controlling embolization and thrombosis in blood vessels. More specifically, the present invention is directed to a blood clot filter, which has improved self-centering capabilities.

BACKGROUND OF RELATED TECHNOLOGY

Blood clots (emboli) which are carried in the blood stream often pose serious threats to a person's health and may lead to death. For that reason, the reduction of such clots and their stabilization and arrest against further migration from the vena cava into the pulmonary circulation are necessary.

A number of types of permanent filters have been designed for this purpose. Generally, these filters are in the form of a frustoconical basket which is attached to the interior of a vein downstream of the area sought to be filtered. One type includes a plurality of wire legs of the same length extending in a generally conical array from a common apex to their free ends which attach to the wall of the vessel, thus forming a cone of revolution with a single plane of contact with the vessel wall. A filter of this type is described in U.S. Pat. No. 3,952,747. The filter shown therein includes sharpened hooks at the free wire ends to permanently anchor the filter by impaling the hooks in the blood vessel. If the hooks engage the cava in a plane perfectly perpendicular to the vena cava, the filter, in theory, would be centered. In reality such perfect deployments rarely occur and so the filter is often deployed in a tipped position, with its apex not coincident with the apex of the vessel.

In an effort to facilitate the correct positioning of these permanent types of filters, U.S. Pat. No. 4,688,553 provides for a self-centering filter where at least some of the legs are, towards their free ends, provided with appendices which extend substantially parallel with the substantially cylindrical wall of the vessel when the filter is inserted within the vessel and whereby each appendix includes a portion extending in the general direction of the apex from which the legs radially diverge and up the vena cava wall. It is the appendices which allow for centering of the filter inside the vein. A disadvantage of this filter is its inability to be easily retrieved. As the appendices of these filters extend in the direction of the apex, the ends thereof would increase interference with the venal wall upon removal thereby rendering removal more difficult.

A general disadvantage of the conical filters of the type described above is that the flexibility of the wires prevents consistent bearing forces from being applied to the vein wall. Moreover, the wire is small, and the bearing surface in contact with the vein is restricted which can lead to trauma and perforations.

Furthermore, filters formed from a conical portion of wire legs are generally difficult to load before emplacement due to the interference of the hooks with each other when the filter is folded into the ejector used for emplacement. Moreover, once the filter is ejected and implanted, it cannot be removed. This often results in permanent placement of the filter in an undesirable location and often requires the placement of another filter at the appropriate location.

Once the thrombotic condition is resolved, typically in a period of 6 weeks to six months, the filter is removed. Since filters of the permanent-type described above are difficult to remove, retrieval is only attempted when medically necessary.

A number of conical filters have since been designed which are both retrievable and self-centering. For example, U.S. Pat. No. 5,152,777 describes a self-centering filter with resilient filter wires designed for temporary emplacement within a vessel. The filter is of the same general conical design as the aforementioned filters except that the filter wires have rounded tips instead of hooks at their free ends to facilitate removal. Moreover, a longitudinally stable stem is permanently affixed to the collar at the vertex of the filter. Once emplaced in the body, the stem remains attached to the filter and serves to keep the -filter centered in the vessel and to facilitate retrieval. This filter therefore has a separate centering portion, consisting of the stem, and a separate trapping/filtering portion consisting of the conical filter wire portion.

A disadvantage of this filter is that it is not firmly anchored to the vessel wall due to the rounded tips at the free wire ends. The filter, even when open, may be moved horizontally within the vessel. This can allow clots to escape the filter. Yet another disadvantage of this filter is that because the stem needs to remain for centering purposes, the patient's immune system suffers the burden of the presence of a larger foreign body. In addition, an obturator needs to be inserted in the lumen of the stem to prevent stagnant blood from accumulating in the lumen and forming potentially dangerous emboli.

It is desirable, therefore, to provide a self-centering vena cava filter which is firmly anchored and retrievable and which does not require a separate centering portion. Moreover, it would be desirable to provide a filter wherein the bearing force is distributed over a larger surface of the venal wall in order to reduce trauma and perforations thereto and to facilitate retrieval of the filter. Finally, it would be desirable to provide a filter which has a reduced profile and which is easier to load into an ejector and to implant within a vein.

SUMMARY OF THE INVENTION

It is an object of the present invention to overcome the disadvantages of the aforementioned filters by providing a retrievable filter that has improved self-centering capabilities in the human vena cava without the need for a separate centering portion and which provides secure anchoring of the filter to the vena cava wall.

It is a further object of the present invention to provide a filter which reduces the incidence of collapsing of the cava, decreases trauma owing to contact pressure on the vein walls and reduces the force necessary to retrieve the filter.

The present invention provides a two-planar filter with improved centering capabilities due to its two planar points of contact with the inner venal wall. Contact at two planes is provided by the contact of two sets of filter wires wherein each set differs in length from the other. In one preferred embodiment, centering capability is additionally improved by providing at least some of the filter wires, preferably in the set of wires of lesser length, with extensions. Barbs, e.g. hooks, are attached to at least one set of filter wires to ensure firm anchoring to the venal wall. Having two planar points of contact has the added benefit of reducing the profile of the filter, which improves ease of emplacement and allows for insertion in veins of lesser diameters. In addition, contact at two different planes reinforces the walls of the vena cava, thus reducing collapse of the vein. Two-planar contact also reduces the trauma to the venal wall owing to contact pressure on the vein walls and reduces the force necessary to retrieve the filter. Lastly, the filter design is versatile in that it allows for filter wires which are straight, corrugated or spiral in design, as well as filter wires which have any combinations of straight, corrugated or spiral portions intermediate their length. Each design presents its own advantages.

DETAILED DESCRIPTION OF THE INVENTION

Figure 1:
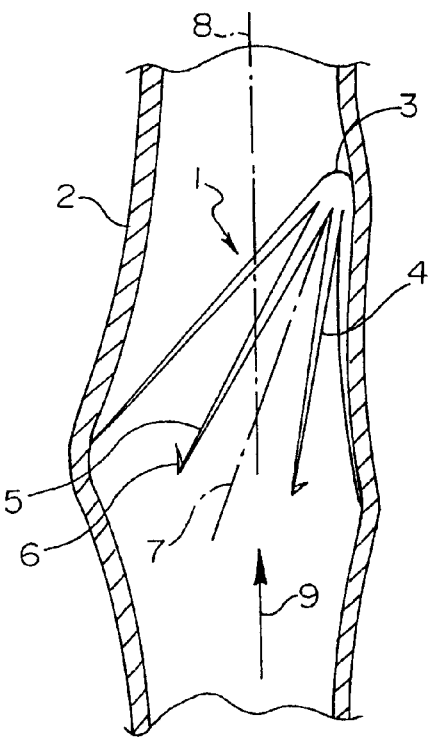
FIG. 1 shows a conical filter typical of the prior art which has been deployed in a skewed position with respect to a vein in which it is implanted.

Referring to FIG. 1, a vena cava filter 1 typical of the prior art is shown positioned inside a vein 2. Filter 1 includes an apex 3 and a plurality of wires 4 extending generally from apex 3 in a conical configuration. As is conventionally known, the distal ends of wires 5 may include thereon hooks 6 which assist in placing and fixing the filter 1 to the vein 2 at a desired location. As mentioned above, and as is shown in FIG. 1, a simple single plane conical filter I of the type shown hereinabove due to its construction has a tendency to be deployed with its axis 7 clearly crosswise in relation to the axis 8 of the vein 2, the direction of blood indicated by the arrow at 9. Deployment of a filter in a skewed position such as shown in FIG. 1 gives the perception that the filter will not work optimally.

Figure 2A:
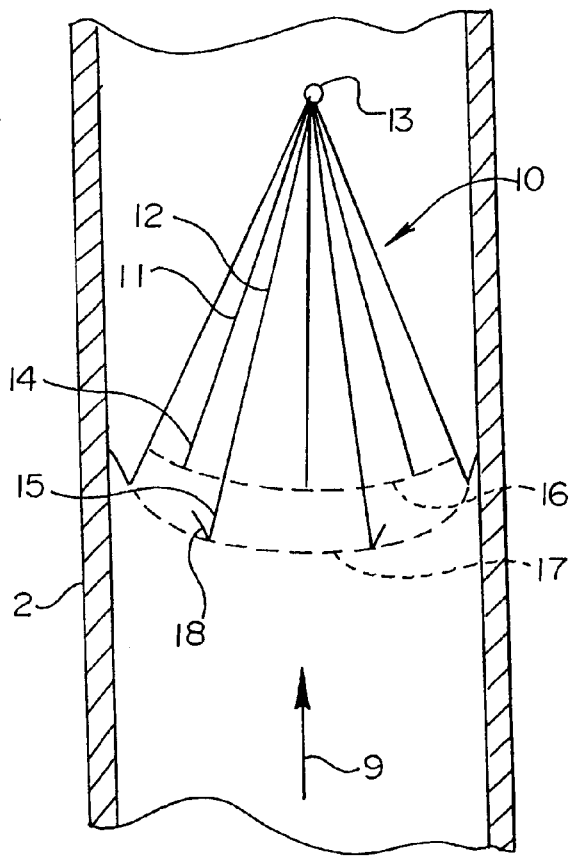
FIG. 2A is generally a longitudinal cross-sectional showing an embodiment of the filter of the present invention positioned in a vein.
Figure 2B:
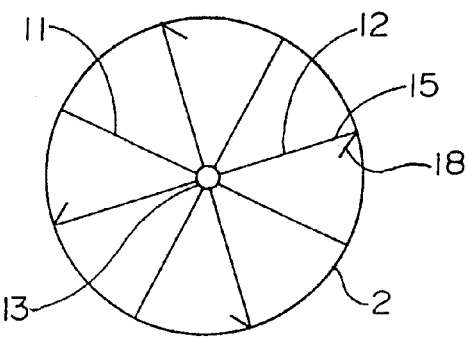
FIG. 2B is a transverse schematic showing of the filter of FIG. 2A.

The present invention provides an improved self-centering filter having a two-planar design. According to one aspect of the invention, FIGS. 2A and 2B show a vena cava filter 10 for placement in a blood vessel such as vein 2. Filter 10, which may be partially formed of stainless steel, titanium, or nitinol, includes two sets of filter wires 11 and 12, each set differing in length from the other. The two sets of filter wires 11, 12 diverge from a common apex 13 at one end and extend radially outwardly therefrom. The sets of filter wires 11, 12 include respectively opposed, free ends 14, 15 attachable to a wall of a blood vessel 2 such that the free ends 14 of one set of filter wires are anchored at a location spaced from the location of anchoring of the free ends 15 of the second set of wires. Thus, the filter wires 11 have ends 14 lying in one place while the filter wires 12 have ends 15 lying in a second place longitudinally spaced therefrom. This arrangement thereby effects a two-planar filter with an emboli-capturing array of filter wires. As shown in FIG. 2A, the filter wires 11 which are of shorter length, contact the venal wall 2 at a first plane 16 and the filter wires of longer length 12 contact the venal wall 2 at a second plane 17 spaced longitudinally in terms of the direction of blood flow which is indicated by the arrow at 9.

As shown in FIGS. 2A and 2B, the wires 11, 12 from each of the two sets extend from apex 13 where they are regularly circumferentially spaced apart one with respect to the other, so as to define a cone of revolution. It is preferred that the shorter wires 11 be inter-digitated with the longer wires 12 so that the filter wires of one length radially alternate with filter wires of a second, different length to form the two planar design.

In the embodiment of FIGS. 2A and 2B, at least one of the sets of filter wires includes anchoring barbs, e.g. hooks 18, at the free wire ends 15 in contact with the vein inner wall at 2 to help secure the filter in position. In this particular embodiment, the hooks are present on the set of filter wires 12 of longer length. However, it is well within the contemplation of the present invention that the hooks may be present on the set of shorter length. It is also an aspect of the present invention that each of the sets of filter wires may include hooks at the free wire ends. Where each of the sets of filter wires include hooks at the free ends, each of the two sets of hooks will be at a different plane, thus allowing for a reduced profile when the filter is compressed. This allows for insertion in veins of smaller diameter and causes less discomfort for the patient during emplacement. In addition, positioning each set of hooks at a different plane provides for an increase in the ease of emplacement due to less interference of the hooks with each other when the filter is folded into the ejector for emplacement.

As shown in FIGS. 2A and 2B the filter wires 11 and 12, extend in a generally linear direction from the apex 13 toward the wall of the vein at 2. The use of linear filter wires results in a reduced profile upon compression, making emplacement within the vein easier and allowing insertion into veins of smaller diameter to be possible.

By providing a two point contact at different planes, the filter has the advantage of improved centering such that the apex of the filter is generally coincident with the axis of the vein. This establishes a single filtering element having two planes of contact with the vein wall, which also provides for centering of the filtering element. In addition, all having contact at two planes reduces the collapsing of the cava by reinforcement of the walls. By increasing the supporting area to include two planes of contact, the contact pressure on the vein walls originating from each of the wire ends decreases, which in turn reduces trauma to the vein walls. In addition, the filter reduces the force that would be required to retrieve the filter should it be medically necessary to do so. A reduction in the force necessary to remove the filter is due to the distribution of the force over two planes of contact. This results in an increase in ease of removal and a decrease in damage to the architecture of the blood vessel upon removal.

Moreover, two planar points of contact with the vessel wall result in less movement of the filter within the vessel due to a greater consistency in the bearing forces applied to the vein wall. Consequently, there is less likelihood that the filter can tilt and allow emboli to pass between the vessel wall and both planar points of contact of the filter wires. Moreover, emboli potentially capable of escaping through the first plane of contact of the filtering element can be trapped at a second plane of contact of the same filtering element.

Figure 3A:
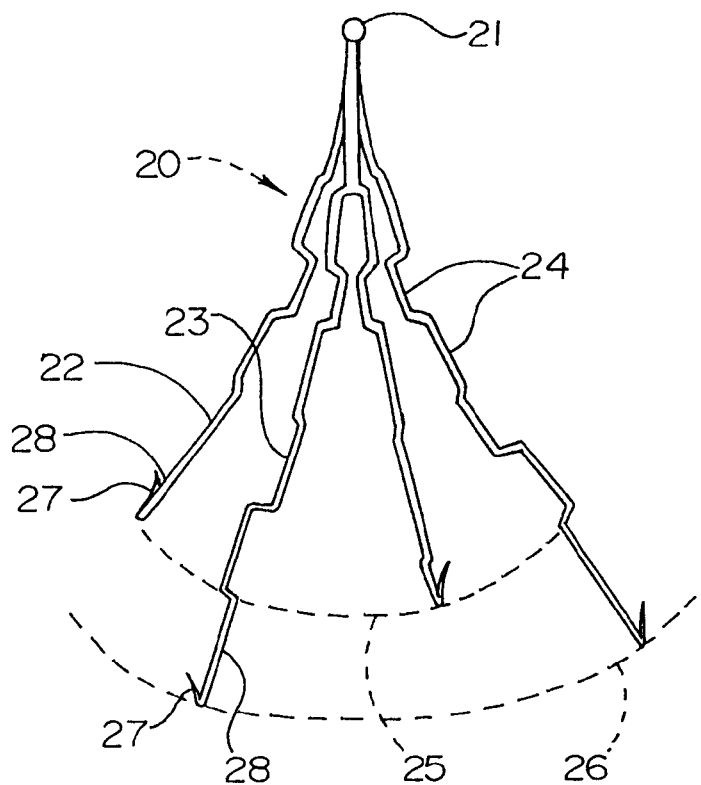
FIG. 3A shows a further embodiment of the filter of the present invention having two sets of filter wires of differing length and containing corrugated U-shaped portions.
Figure 3B:
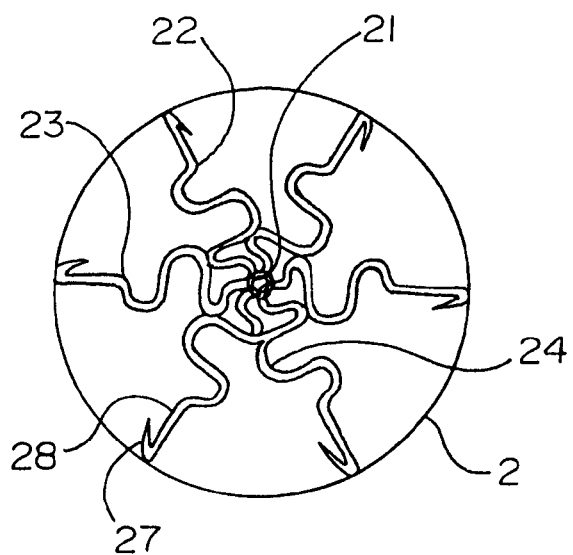
FIG. 3B is a top plan view of the embodiment of the present invention of FIG. 3A.
Figure 4A:
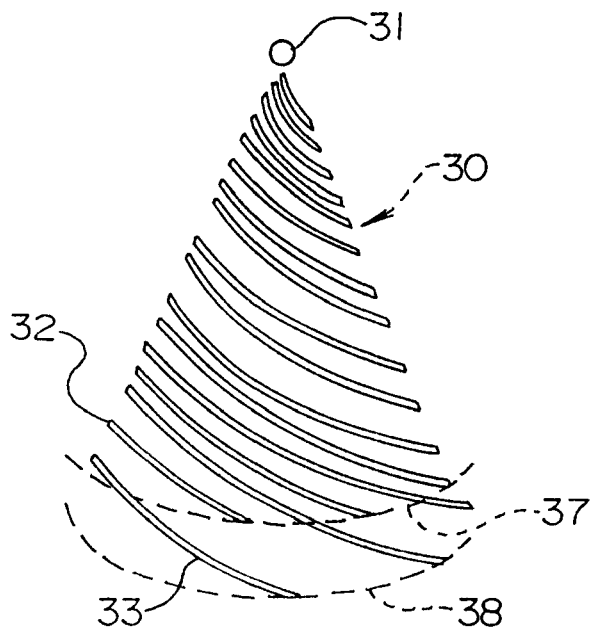
FIG. 4A shows an additional embodiment of the filter of the present invention having two sets of spiral filter wires of differing length.
Figure 4B:
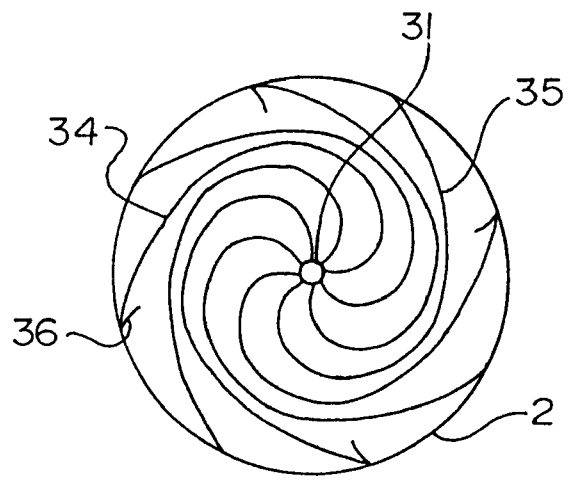
FIG. 4B is a top plan view of the embodiment shown in FIG. 4A.

In another aspect of the present invention, a further embodiment is shown in FIGS. 3A and 3B. In this embodiment, a two plane filter 20 includes a central apex 21 and two sets of filter wires 22, 23 extending therefrom. Each of the filter wires 22, 23 extend in a corrugated fashion from the apex 21 of the filter. The corrugated portions 24 may be of a general U-shaped design as depicted in FIGS. 3A and 3B. Alternatively, the corrugated portions 24 may simply have multi-angular linear segments. It can be appreciated that, wherein the angles depicted in FIGS. 3A and 3B are generally right angles, any angles can be used to form the corrugated portions. Corrugations, in general, provide for more effective fibrinolysis of the emboli. In the specific embodiment shown in FIGS. 3A and 3B, the filter wires 22 of shorter length make contact with the venal wall 2 at a first plane 25 whereas the filter wires 23 of longer length make contact at a second plane 26. As shown in FIGS. 3A and 3B, each of the filter wires contain hooks 27 at their free ends 28 for anchoring to the venal wall shown at 2 in FIG. 3B. Alternatively, only one of the two sets of filter wires may include hooks. While the corrugated portions 24 in FIGS. 3A and 3B are shown on both sets of filter wires 22, 23, it may be appreciated that the corrugated portion 24 may be used on only one set of the filter wires 22, 23. It is also under the contemplation of the present invention that at least one of the filter wires may include linear portions interrupted by corrugated portions intermediate the length thereof A still further embodiment of the invention is shown in FIGS. 4A and 4B. In the embodiment shown therein a two plane filter 30 includes an apex 31 having a plurality of filter wires wherein at least one of the filter wires, represented by 32, 33, 34 and 35 extends in a spiral fashion from the apex 31. In FIG. 4B, hooks 36 are positioned on a set of filter wires of a set length at 34. Hooks at 36 allow anchoring of the filter to the inner venal wall at 2. In FIG. 4B, wires 34 with hooks 36 radially alternate with wires 35 of a different length containing no hooks. However, in another aspect of the present invention, each set of wires of a different length may include hooks at the free wire ends. In FIG. 4A, wires of a shorter length, represented by 32 make contact with the venal wall at a first plane 37, whereas the longer wires, represented by 33, make contact at a second plane 38. Although not shown in FIG. 4A, hooks may be positioned on one of the sets of filter wires.

It is further contemplated that at least one of the spiral filter wires can, intermediate its length, contain any combination of generally linear, spiral and corrugated portions.

Figure 5:
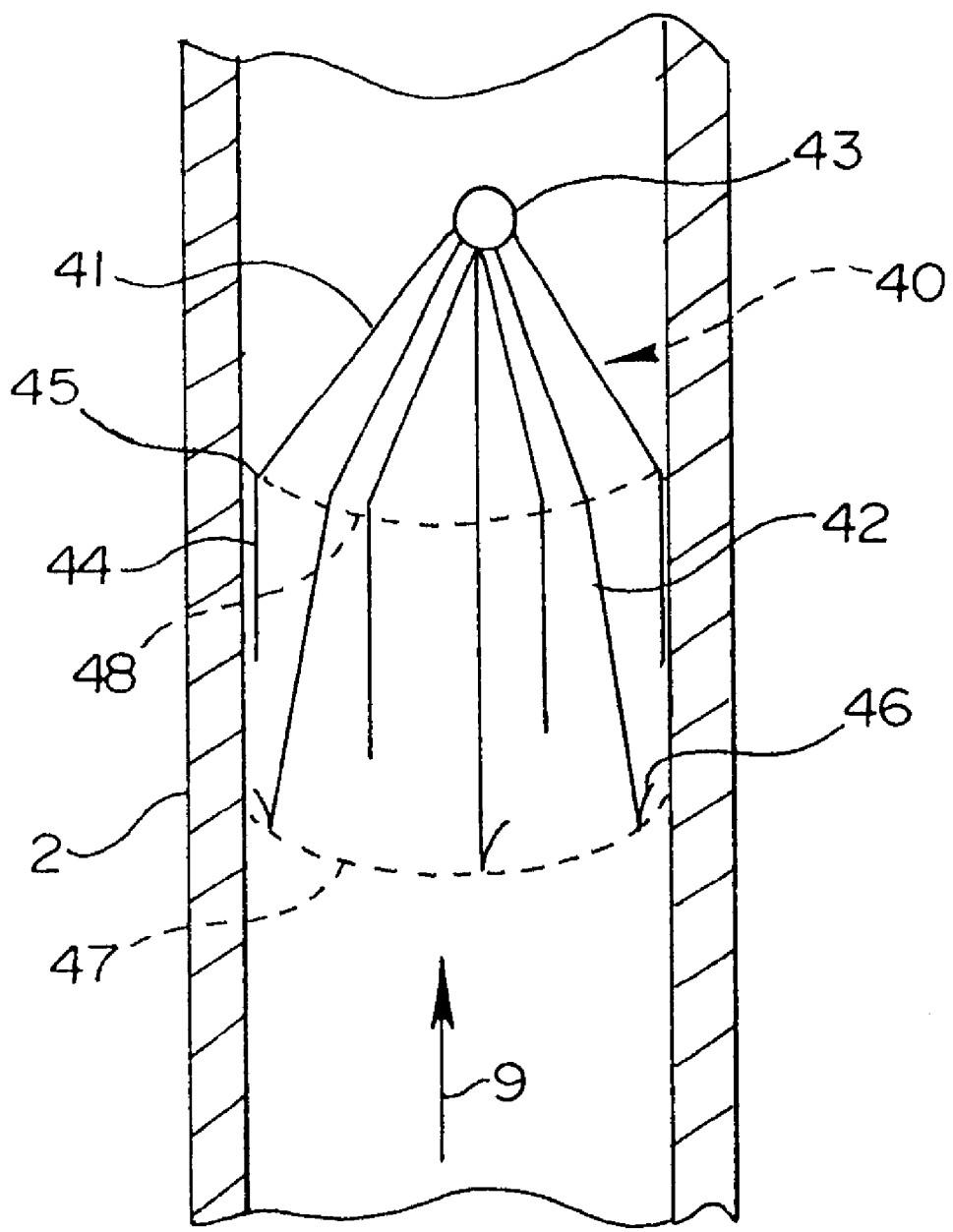
FIG. 5 shows a still further embodiment of the filter of the present invention.

Another embodiment of the present invention is shown in FIG. 5. A two plane filter 40 includes first and second sets of filter wires 41 and 42 extending from a common apex 43. A set of filter wires 41 includes one wire extension 44 extending from the distal end 45 thereof Extensions 44 may be integrally formed with wires 41. In this way, when the filter is inserted into the vein, the extensions 44 are applied against the walls of the vein 2 and compel the filter to adopt a position with its axis generally coincident with the axis of the vein, thus improving its centering upon deployment and providing additional stability. Moreover, the extensions provide an even broader supporting area, which decreases the trauma owing to contact pressure on the vein walls. It is also noteworthy that extensions may also favor satisfactory hooking of the filter in the vein and better tolerance, making it possible to reduce the aggressiveness of the anchoring hooks as a result of the larger anchoring surface which the appendices offer. As shown in FIG. 5, hooks 46 are provided on the wires 42 of longer length for anchoring at plane 47. These wires radially alternate with wires 41 of a shorter length which contact the wall 2 at a different plane at 48. The direction of blood flow is indicated by the arrow at 9.

In yet another aspect of the present invention, the extensions may include anchoring hooks at their free ends.

The provision for extensions 44, which extend in a downward direction with the vessel wall increases the ease of removal of this filter relative to a filter-type with extensions extending in a direction toward the apex of the filter. This is because the ends of the downwardly-directed extensions 44 would not be expected to interfere with the venal walls upon removal.

According to a characteristic of one preferred embodiment of the invention, the filter wires 41 provided with the extensions 44 are shorter than filter wires 42. In this way, when the filter is introduced into the vein the wires 41 provided with the extensions 44 are the first to be applied against the inner wall of the vein and so center the filter before the other longer filter wires 42 are deployed and become hooked into the inside of the vein.

While the extensions 44 are preferably integrally formed with filter wires 41, it is within the contemplation of the present invention to form extensions 44 as separate members which are affixed to the opposed ends of the shorter of the two sets of filter wires. While the extensions 44 are integrally formed, each extension 44 can be a bent portion located at the distal end 45 of the shorter of the two sets of filter wires 41 as depicted in FIG. 5.

Various changes to the foregoing described and shown structures would now be evident to those skilled in the art. Accordingly, the particularly disclosed scope of the invention is set forth in the following claims.

What is claimed is:

1. A self-centering vascular filter for placement in a blood vessel comprising:

a first and a second plurality of elongate filter wires having a common apex at one end and extending radially outwardly therefrom to an opposed attachment end attachable to a wall of said vessel, said first and second plurality of filter wires being spaced apart a distance selected to retard migration of emboli in said vessel; and said first plurality of filter wires having a first length and said second plurality of filter wires having a second length different from said first length so that said attachment ends of said first plurality of filter wires are anchored at a location spaced from the location of anchoring of said attachment ends of said second plurality of filter wires.

2. A self-centering vascular filter of claim 1 wherein at least one of said plurality of filter wire attachments ends includes anchoring barbs.

3. A self-centering vascular filter of claim 2 wherein said anchoring barbs include hooks.

4. A self-centering vascular filter of claim 2, wherein said barbs of said first plurality of filter wires are located on a different plane from said barbs of second plurality of filter wires, whereby said filter presents a reduced profile when positioned in a compressed state.

5. A self-centering vascular filter of claim 1 wherein said filter wires of said first plurality radially alternate within said filter wires of said second plurality.

6. A self-centering vascular filter of claim 1 wherein at least one of said filter wires extends in a generally linear direction from said apex.

* * * * *